United States Patent [19]

Vlcek

[11] 4,215,567
[45] Aug. 5, 1980

[54] METHOD AND APPARATUS FOR TESTING A PRODUCTION STREAM

[75] Inventor: Richard J. Vlcek, Englewood, Colo.

[73] Assignee: Mobil Oil Corporation, New York, N.Y.

[21] Appl. No.: 49,512

[22] Filed: Jun. 18, 1979

[51] Int. Cl.² .................. G01N 1/10; G01N 33/28
[52] U.S. Cl. ................................ 73/61.1 R; 73/19; 73/422 R
[58] Field of Search .......... 73/422 R, 422 TC, 421 B, 73/61.1 R, 61 R, 19

[56] References Cited

U.S. PATENT DOCUMENTS

| | | | |
|---|---|---|---|
| 2,225,798 | 12/1940 | Price | 73/422 R |
| 2,306,606 | 12/1942 | Hirsch | 73/422 R |
| 3,638,476 | 2/1972 | Paterson | 73/422 R |
| 3,638,498 | 2/1972 | Nelms | 73/422 TC |

*Primary Examiner*—S. Clement Swisher
*Attorney, Agent, or Firm*—C. A. Huggett; Drude Faulconer

[57] ABSTRACT

A method and apparatus for testing a production stream comprised of oil, water, and gas flowing through a conduit to determine the percentages of oil, water, and gas in the stream. A sample portion of the production stream is pumped through a sample line into a sample chamber where it is heated and allowed to set for a retention period to substantially separate the sample portion into oil and water layers. Gas that evolves from the sample portion is vented from the chamber. At the end of the retention period, the sample portion is pumped back through the sample line into the conduit. As the sample portion flows through the sample line the oil and water content of the sample and the volume of the sample are measured to determine the oil and water percentages in the sample portion. Also, the volume of the sample portion is measured as it is pumped through the sample line into the sample chamber and by comparing this volume with the volume of the sample portion pumped back into the conduit, the gas-liquid ratio of the sample portion can be determined.

15 Claims, 3 Drawing Figures

METHOD AND APPARATUS FOR TESTING A PRODUCTION STREAM

BACKGROUND OF THE INVENTION

The present invention relates to the testing of a fluid stream and more particularly relates to a method and apparatus for automatically testing a production stream of crude oil, water, and gas from a well to determine the percentages of each component in the stream.

A production stream from an oil producing well is normally comprised of a mixture of gas, crude oil, and water. Since royalty payments are based on the crude oil produced, it is necessary not only to meter the total volume of fluid produced from a well, but also to determine what percentage of produced fluid is crude oil. This normally is done by carrying out periodic laboratory tests on samples of the production stream taken at or near the wellhead.

The testing of a production stream is usually time consuming and may be complicated by (1) the composition of the crude oil itself, (2) small production rates, and/or (3) high water contents. For example, the production from the Belridge and San Ardo Fields in California is from heavy, viscous oil reservoirs which are produced with the aid of steam injection and in-situ combustion. The production streams from these wells are typically ones having highly viscous crude, a high water cut, and some gas. Further the production rates of the individual wells vary over a wide range, e.g. from 3 barrels per day to several hundred barrels per day. The oil contents vary from 2-50% and temperatures range from 50°-200° F.

Several procedures have been proposed and/or used for testing production streams of the type described above. At Belridge, one such procedure commonly called "3 Way AWT" (Automatic Well Tester) involved flowing a test stream from a well into a relatively large horizontal pressure vessel wherein the produced fluid was allowed to separate into gas, oil, and water layers. The free gas was vented and the oil/water and free water were independently measured as they were returned to the main production line through separate lines. Due to problems with (a) maintaining the oil/water and free water interface (essential for proper operation), (b) the unreliable dump valve controls, and (c) sand buildup, this testing procedure was found to give erratic data in Belridge and was discontinued after short use although it is still in use in other areas.

Another method, commonly called "open tank AWT", was also tested at Belridge and consequently rejected. This procedure involves flowing the production fluid through a test line into a large open tank, i.e., 100-barrel tank, where it is allowed to accumulate for the entire well test period. Under atmospheric pressure, free and solution gas escapes out of the fluid and is removed from the top of the tank. The oil and water are pumped from the tank at the end of the test period through an outlet line to the main production line in which an inserted flowmeter, in conjunction with a net oil computer, determines the oil and water production of the well during the test period. This procedure has a number of drawbacks involved in its use. First, it requires substantial surface area in the proximity of the well test manifold to accommodate the large tank (e.g. 100-barrel) and the associated pump station. Also, it has been found that this technique creates significant flow surges downstream at the associated oil treating facilities. Another major problem arises in handling the tested crude oil due to the increased viscosity of the heavy crude caused by the cooling down of the crude as it sets in the open tank. Further, this procedure may sometimes give a distorted picture about a particular well's performance due to the different back pressure when pumping into the main production line as against testing into the open tank. And last, due to the large volume (100 barrels) required for testing high producing wells, the test results on low producing wells, e.g. 3 barrels per day (126 gallons per day), are unreliable or impossible to obtain.

SUMMARY OF THE INVENTION

The present invention provides a method and apparatus capable of testing production streams comprised of heavy, viscous crude oil, high water cuts, and gas from wells having either high or low production rates to thereby determine the percentages of oil, water, and gas in the tested production stream.

In accordance with the present invention, production streams from numerous wells are fed through selector valves to a main production line. Upon receipt of a programmed signal, the selector value diverts one of the production streams into a test line. If desired, the selected stream passes through a separator in which free gas is removed from the stream. From the separator, the stream passes through a gross meter which measures the total flow rate of the selected stream before it is returned to the main production line.

Positioned in the test line downstream of the gross meter is a probe which is adapted to divert a sample portion of the selected stream into a sample line. A programmed signal opens a valve in the sample line and starts a reversible pump which, in turn, pumps a sample portion independent of the well's total production, e.g. 5 to 10 gallons, from the test line into a sample chamber. Means is provided to measure the volume of the sample portion as it is pumped to the sample chamber. The pump will operate for a preset constant timed interval or until the chamber contains a desired optimum amount of sample. When this time interval elapses, the valve closes in the sample line and the pump stops.

The sample portion is allowed to set in the sample chamber for a programmed period of time during which it is heated by heating elements to a set temperature. The heating helps the sample portion to at least partially divide into oil and water layers and to drive gas out of solution. The gas is vented from the top of the sample chamber. At the end of this timed period, a programmed signal opens the valve in the sample line and the pump pumps the sample portion from the sample chamber back into the test line.

As the sample portion is pumped back through the sample line, the oil and water contents of the sample are monitored and this data are recorded on oil and water accumulator cards in a remote terminal unit (RTU). Also, the volume of the sample portion is again measured and this data is also fed to the RTU. The oil and water content data and the volume data when combined with the gross meter data, determine the final percentages of oil, water, and gas in selected stream. When all of the sample portion has been pumped out of the sample chamber, a float switch closes the valve in the sample line and stops the pump. The complete test cycle is now over and the test unit is ready to test another production stream. Although the invention has been mentioned as capable of testing heavy or viscous oil production, it should be recognized that it can be used to test any oil production streams. The actual construction, operation, and the apparent advantages of the present invention will be better understood by referring to the drawings in which like numerals identify like parts.

DESCRIPTION OF THE PREFERRED EMBODIMENTS

Figure 1:
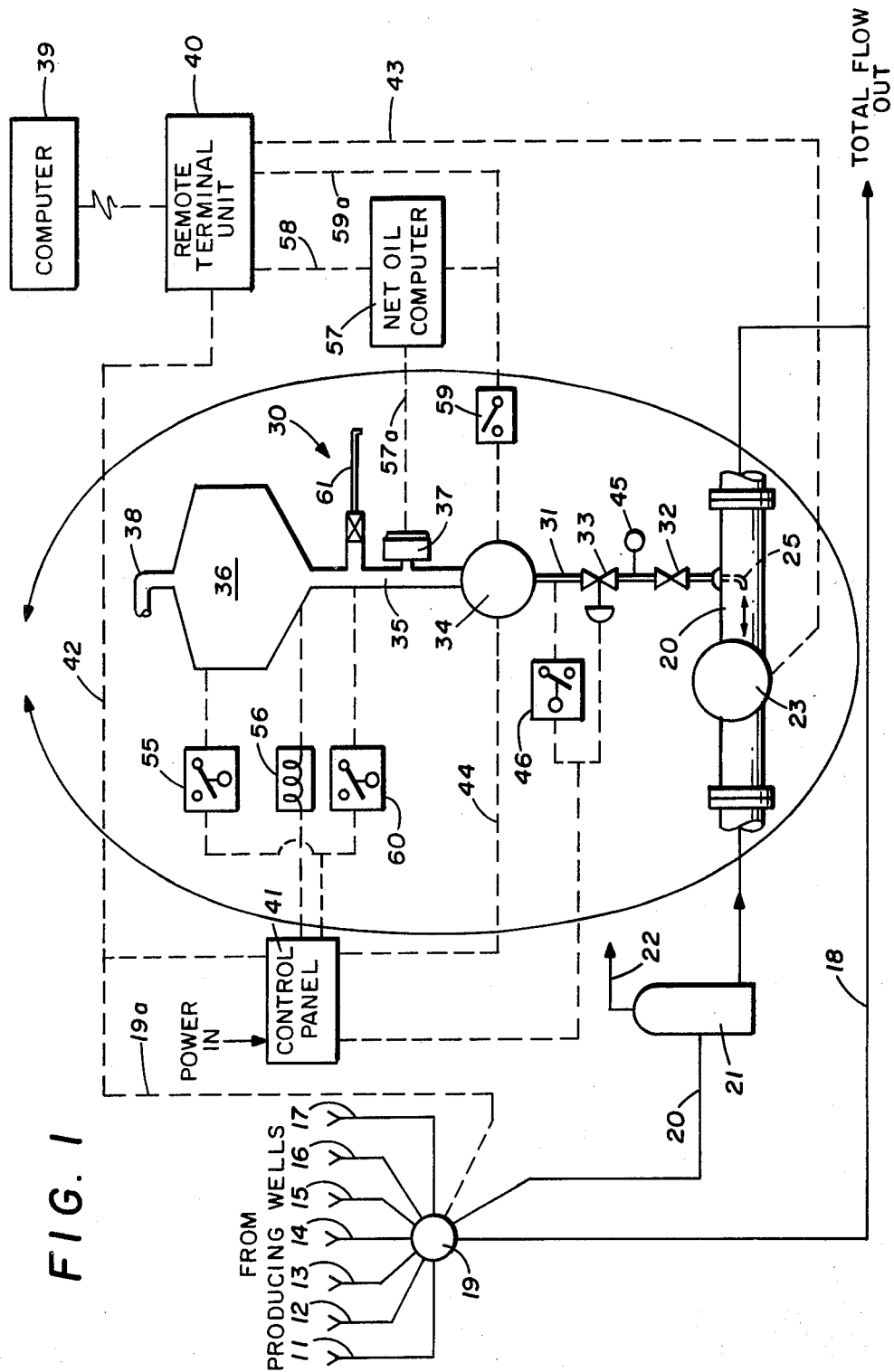
FIG. 1 is a schematic view, having a portion thereof enlarged, of the present invention within a system for testing a production stream selected from one of a plurality of wells.

Referring more particularly to the drawings, FIG. 1 discloses the automatic well testing system 10 of the present invention. Individual production streams 11-17, inclusive, from a plurality of wells are fed through a remotely operated, multi-position selector value 19 into a main production line 18. Valve 19, upon actuation, selects one of the production streams and diverts it into test line 20.

The selected stream flows into separator 21 in which free gas is separated from the stream and is removed through line 22. The selected stream then flows from separator 21, through a gross meter 23 (e.g. 2"-3" positive displacement flowmeter with magnetic pulse pick up, such as Barton Model 308, ITT Barton, City of Industry, Calif.) which measures the total flow rate of the selected stream, and then into main production line 18. Check valves (not shown) prevent reverse flow.

Positioned in test line 20 downstream of meter 23 is tubular probe 25 which is adapted to divert a sample portion of the selected production stream from test line 20 into Automatic Well Test (AWT) unit 30 wherein the oil, water, and gas content of the sample portion is measured before it is returned to test line 20. The overall structural arrangement of system 10 having been briefly described, a more detailed description of AWT unit 30 and the testing method carried out thereby will now be set forth.

Preferably, the entire test procedure of the present invention will be fully automated and controlled by the computer 39 through remote terminal unit (RTU) 40 (FIG. 1) which, as understood by those skilled in the art, can be located at substantial distances from AWT unit 30. Although the present invention will be described as fully automated, it will be readily understood that all of the functions may be performed manually or semi-automatically depending on the oil field operations set-up and the degree of automation desired.

A signal from programmed computer 39 is fed through RTU 40 and transmitted through path 42, 19a, to selector valve 19 to select a particular production stream from wells 11-17 for testing. It is understood that any programmed sequence can be followed for testing the wells so that the order of testing can be varied as desired. The selected stream flows through test line 20 and into separator 21 where free gas is removed from the stream.

Figure 2:
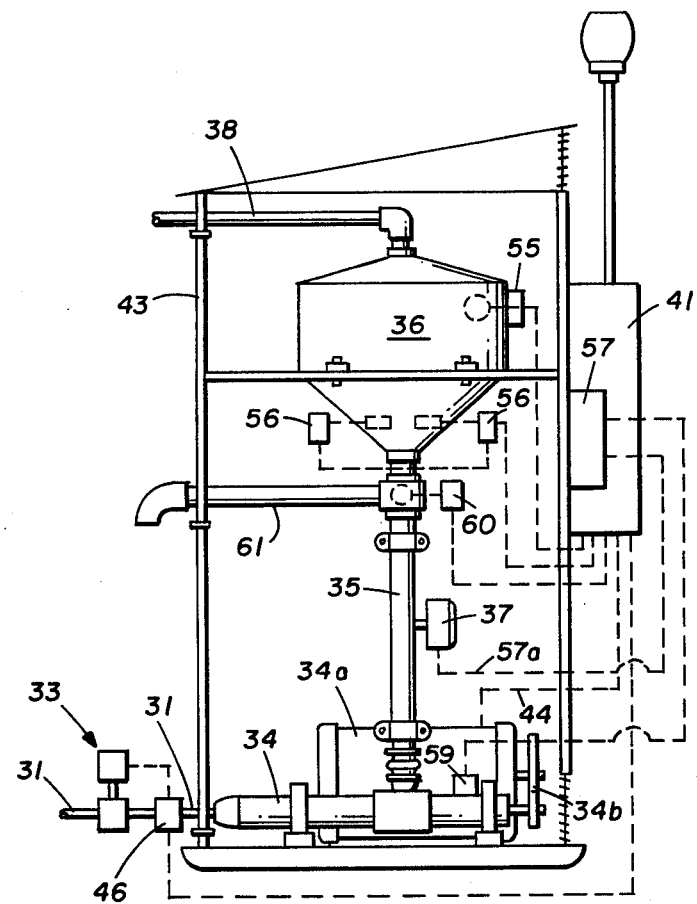
FIG. 2 is an elevational view of the automatic test unit of the present invention.
Figure 3:
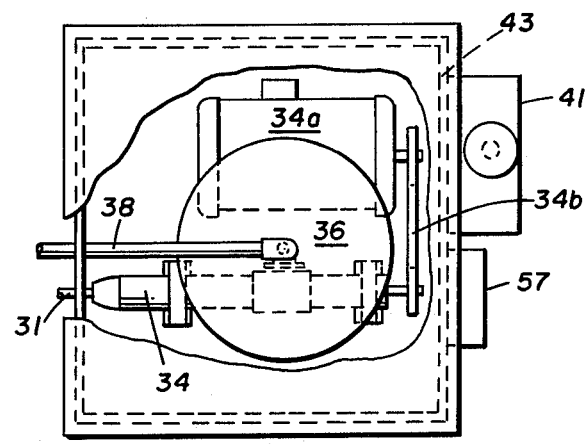
FIG. 3 is a plan view of FIG. 2.

The production of the well on test flows through gross meter 23 which measures the total flow rate of the well being tested. The output of meter 23 can be directly recorded on a field recorder (not shown) but is preferably transmitted as pulses through path 43 to RTU 40. As test line 20 fills with the selected stream, solenoid valve 33 in line pressure line 31 is energized from control panel 41, illustrated as being mounted on frame 43 (FIG. 2) of AWT unit 30, to allow a sample portion of the selected stream to flow through probe 25 into line 31 and to the inlet of pump means 34. Manual valve 32 in line 31 is always open during testing and is closed only for maintenance, repair, or replacement of AWT unit 30. Solenoid valve 33 is energized for a timed interval, e.g. 2 minutes, to allow the pressure in line 31 to build to a minimum operating valve, e.g. 40 psig. This pressure will be sensed by pressure-sensitive switch 46 in line 31 and if at the end of the timed interval, the pressure is at a value equal to or above the minimum operating pressure, switch 46 will maintain solenoid valve 33 in an open position and a signal will be transmitted to start pump 34. If the pressure in line 31 is below the minimum operating pressure at the end of the timed interval or any time during pump-in cycle, solenoid valve 33 is de-energized and the test procedure for the selected well is terminated. Any sample portion is pumped back without monitoring and the unit is ready to receive start command for testing the next well. This insures that there is sufficient fluid in line 31 for pump means 34 to operate without damage as would be the case if the selected well had been shut in before the testing program could be changed or ceased to pump during the test period. Also, a visual pressure gauge 45 may be provided in line 31 for on-site determination that sufficient fluid is present in line 31 before a test operation is commenced.

With above mentioned pressure prerequisites in line 31 at the end of the timed interval, a signal is transmitted from panel 41 through line 44 to a reversible motor 34a to start pump 34. Pump 34 is preferably a rotary-driven, progressing cavity pump with oversized rotor, e.g. Moyno 6M1 pump, manufactured by Robbins & Myers, Moyno Pump Div., Springfield, Ohio, and is capable of pumping fluid in one direction when rotated clockwise and in the other direction when rotated counterclockwise. Reversible motor 34a, mounted on frame 43, drives pump 34 in the desired direction by means of belt 34b.

Pump 34 pumps the fluid in line 31 through sample line 35 into sample chamber 36. The volume of the fluid pumped by pump 34 is measured by means of magnetic pulse unit 59 which counts the revolutions of the rotating shaft of pump 34. These pulses are transmitted through path 59a to RTU 40 which is programmed to record the volume of the pumped sample portion (note: each revolution of pump 34 corresponds to a constant volume of fluid) and store this data for a purpose to be described below.

Pump 34 will operate for a programmed timed interval, e.g. 15 minutes, during which time chamber 35 will be filled with a desired volume of sample fluid, e.g. 5 to 10 gallons. At the end of the timed interval pump means 34 stops and solenoid valve 33 closes. If the volume of fluid pumped into chamber 35 exceeds the desired volume before the timed interval has elapsed, upper level switch 55 near the top of chamber 35 will be actuated by the fluid level and will transmit a signal to panel 41 which in turn will relay a signal to automatically close solenoid valve 33 and stop pump means 34. The unit will indicate alarm status and cannot be remotely restarted.

The sample fluid in chamber 36 is allowed to set for a defined retention period, e.g. 15 minutes. Immersion heaters 56, e.g. two 750-watt heating elements with a thermostatic switch (not shown), are energized by a programmed signal from panel 41 to heat the sample fluid to a standardized temperature, e.g. 180° F. By heating the sample fluid from each tested well to the same temperature, a more accurate comparison of the various production wells can be realized. Also, the heating of the sample fluid aids in separating the fluid into oil and water layers and in escaping the solution gas from the liquid. The free gas is removed from chamber 36 through vent 38. Further, the heating of the fluid keeps heavy, viscous oil mobile enough to insure that it will readily flow from chamber 36 at the end of the retention period.

When the retention period elapses, programmed signals are transmitted from panel 41 to turn off heaters 56 to start motor 34a to drive pump 34 in the opposite direction, and to open solenoid valve 33 for flow. Pump 34 pumps the sample fluid from chamber 36, through sample line 31, and back into test line 20. As the sample fluid flows through sample line 35, it passes means 37 which measures the oil/water and the free water ratios of the fluid at that point and transmits this data to monitor means 57, e.g. electronic basic water and sediment (BS&W) monitor. Means 37 is preferably a capacitance-type probe which detects the presence of water by the change in dielectric constant of fluid as it contacts sensing elements, i.e. electrodes, of the probe. The package of probe 37 and monitor means 57 is well known in the art and is commonly called a net oil computer, e.g. Model CM510, manufactured by Kobe Systems Division, Odessa, Tex.

As the sample fluid is pumped back into test line 20, its volume is again measured by magnetic pulse unit 59 which transmits these pulses to both BS&W monitor 57 and directly through line 59a to RTU 40. As understood by those skilled in the art, BS&W monitor 57 combines the data from probe 37 and the volume data from unit 59 and generates pulses which are recorded on respective oil and water count accumulator cards (not shown) in RTU 40.

Computer 39 scans the oil and water accumulator cards in RTU 40 and combines this data with the volume data from gross meter 23 to calculate the actual percentages (i.e. cuts) of water and oil in the tested production stream.

Computer 39, also, compares the volume data of the sample portion as it is pumped from chamber 36 with the previously stored volume data obtained as the sample portion was pumped into chamber 36 to determine the gas-liquid ratio of the sample fluid. Note, there will be a loss in volume due to the gas vented from chamber 36. This final water, oil, and gas-liquid ratio data is the actual oil, water, and gas content of the total production stream from the selected well for the test period from which royalties on a particular well can be calculated.

When all of the sample portion is pumped from sample chamber 36, lower level switch 60 will signal control panel 41 which, in turn, transmits a stop signal to pump 34 and a signal to close solenoid valve 33. The unit timer completes the cycle run independently of the pump status. At this point, the test operation is complete and unit 10 is now ready for testing another production stream.

If for any reason a test operation must be stopped before it is completed, chamber 36 can be drained through drain 61 or by manually energizing the pump motor. Drain 61 can also be used to take an actual sample of the fluid in chamber 36 if the need ever arises.

What is claimed is:

1. A unit for testing a production stream flowing through a conduit wherein said production stream is comprised of crude oil, water, and gas, said unit comprising:
   a sample line;
   a sample chamber connected to one end of said sample line;
   means adapted to be positioned in said conduit to divert a sample portion of said production stream from said conduit into said sample line;
   pump means for pumping said sample portion from said conduit into said sample chamber when operated in one direction and for pumping said sample portion from said sample chamber back into said conduit when operated in a second direction; and
   means for measuring the oil and the water contents of said sample portion as it is pumped from said sample line back into said conduit.

2. The unit of claim 1 including:
   means associated with said sample chamber for heating said sample portion while said sample portion is in said sample chamber.

3. The unit of claim 1 including:
   means for venting gas from the top of said sample chamber.

4. The unit of claim 3 wherein said means for pumping said sample portion comprises:
   a reversible, progressing cavity rotary pump.

5. The unit of claim 4 wherein said means for measuring the oil and the water contents of said sample portion comprises:
   a capacitance probe positioned in said sample line which allocates signals representative of the oil and the water contents of the sample portion as it passes said probe;
   means for measuring the volume of the sample portion as it is pumped back into said conduit and generating signals representative of said measured volume; and
   means for combining said probe signals representative of said oil and said water contents and said signal representative of said measured volume to determine the oil and the water percentages, respectively, of said production stream.

6. The unit of claim 5 wherein:
   said capacitance probe comprises:
   a basic sediment and water monitor; and wherein
   said means for measuring the volume of sample portion comprises:
   a magnetic pulse unit associated with said rotary pump adapted to count the revolutions of said rotary pump.

7. The unit of claim 6 including:
   a solenoid-operated valve position in said sample line downstream of said pump for opening and closing said sample line to flow in response to a programmed signal and sample line pressure.

8. The unit of claim 7 including:
   an upper level switch means positioned near the top of said sample chamber for stopping said pump and closing said solenoid-operated valve when the volume of said sample portion in said sample chamber exceeds a desired volume.

9. The unit of claim 8 including:

a lower level switch means positioned below the bottom of said sample chamber for stopping said pump and closing said solenoid-operated valve when all of said sample portion has been pumped from said sample chamber.

10. A method for testing a production stream comprised of crude oil, water, and gas flowing through a conduit, said method comprising:

pumping a sample portion of said production stream from said conduit through a sample line and into a sample chamber;

allowing said sample portion to set in said sample chamber for a defined period of time;

pumping said sample portion from said sample chamber, through said sample line, and back into said conduit after said defined period of time has elapsed; and measuring the water and the oil content of said sample portion as it is pumped from said sample chamber back into said conduit.

11. The method of claim 10 including:

heating said sample portion to a defined temperature while the sample portion is setting in said sample chamber.

12. The method of claim 11 including:

venting gas from said sample chamber that may separate from sample portion while said sample portion is setting in said sample chamber.

13. The method of claim 12 including:

removing free gas from said production stream before said sample portion is pumped into said sample chamber.

14. The method of claim 12 wherein said step of measuring the water and the oil content of said sample portion comprises:

passing said sample portion by a capacitance probe which measured the oil and the water content of the sample portion adjacent said probe and generating data representative of said oil and said water contents;

accumulating said oil and said water content data;

measuring the volume of said sample portion as it is pumped from said sample chamber back into said conduit and generating data representative of said volume; and combining said oil and said water content data with said volume data to determine the oil and the water content of said sample portion.

15. The method of claim 14 including:

measuring the volume of said sample portion as it is pumped from said conduit into said chamber and generating data representative of said volume; and combining said volume data generated as the sample portion is pumped into said sample chamber with said volume data generated as said sample portion is pumped from said sample chamber back into said conduit to determine the gas-liquid ratio of said sample portion.

* * * * *